(12) United States Patent
Dittrich et al.

(10) Patent No.: US 6,191,296 B1
(45) Date of Patent: Feb. 20, 2001

(54) CONTINUOUS METHOD OF MANUFACTURING CHLORINE-FREE TETRAALKOXYSILANES

(75) Inventors: Uwe Dittrich, Radebeul; Frank Steding, Marl; Reinhard Mueller, Nuenchritz, all of (DE)

(73) Assignee: Hüls Aktiengesellschaft, Marl (DE)

( * ) Notice: Under 35 U.S.C. 154(b), the term of this patent shall be extended for 0 days.

(21) Appl. No.: 09/245,301

(22) Filed: Feb. 5, 1999

(30) Foreign Application Priority Data

Feb. 6, 1998 (DE) .............................................. 198 04 731

(51) Int. Cl.$^7$ ................. C07F 7/08; C07F 7/18; C07F 7/04

(52) U.S. Cl. ............................................................. 556/470

(58) Field of Search ............................................. 556/470

(56) References Cited

U.S. PATENT DOCUMENTS

| | | | |
|---|---|---|---|
| 4,211,717 | * 7/1980 | Emblem et al. | 556/470 |
| 4,224,234 | 9/1980 | Flick et al. | |
| 4,288,604 | * 9/1981 | Magee et al. | 556/470 |
| 4,762,939 | * 8/1988 | Mendicino | 556/470 |
| 5,103,034 | * 4/1992 | Cho et al. | 556/470 |
| 5,166,384 | * 11/1992 | Bailey et al. | 556/466 |
| 5,728,858 | * 3/1998 | Lewis et al. | 556/470 |
| 5,783,720 | * 7/1998 | Mendicino et al. | 556/470 |

FOREIGN PATENT DOCUMENTS 0 127 951  12/1984  (EP) .
0 225 137   6/1987  (EP) .

* cited by examiner

Primary Examiner—Paul F. Shaver
(74) Attorney, Agent, or Firm—Oblon, Spivak, McClelland, Maier & Neustadt, P.C.

(57) ABSTRACT

Chlorine-free tetraalkoxysilanes of formula (I)

$$(R^1O)_4Si \qquad (I)$$

wherein $R^1$ is, independently in each instance, an unbranched, branched, and/or cyclic $C_{1-6}$ hydrocarbon group is continuously manufactured by a process, comprising:

reacting metallic silicon powder with a monohydric alcohol in the presence of a basic catalyst comprising a mixture of:

(a) at least one compound of formula (II)

$$[R^2O-(R^3O)_m]_nSi)OR^1)_{4-n} \qquad (II)$$

(b) at least one compound of formula (III)

$$R^2O-(R^3O)_m-M, \text{ and} \qquad (III)$$

(c) at least one compound of formula (IV)

$$R^2O-(R^3O)_m-H \qquad (IV)$$

wherein $R^1$ is as defined above;
$R^2$ represents, independently in each instance, a $C_{1-10}$ hydrocarbon group, or hydrogen;
$R^3$ represents, independently in each instance, a $C_{1-4}$ hydrocarbon group;
M represents an alkali metal selected from the group consisting of Li, Na, and K;
m is zero or a number in the range of 1–20; and
n is zero or a number in the range of 1–4; further comprising:
charging said catalyst in advance to a continuously operating reactor to which at elevated temperature is also continuously added metallic silicon powder and the alcohol; and then
separating the reaction mixture in a first column, in which gaseous hydrogen is discharged from the top, high-boiling catalyst is returned to the reaction mixture in said reactor, and low-boiling components are sent to a second separation column in which the tetraalkoxysilanes of formula (I) are separated, and low-boiling alcohol(s) present is/are returned to the reactor.

15 Claims, 1 Drawing Sheet

CONTINUOUS METHOD OF MANUFACTURING CHLORINE-FREE TETRAALKOXYSILANES

BACKGROUND OF THE INVENTION

1. Field of the Invention

The present invention relates to a continuous method of manufacturing chlorine-free tetraalkoxysilanes from metallic silicon powder and alcohol in the presence of a liquid, basic catalyst mixture with improved selectivity and improved space-time yield.

2. Description of the Background

Methods of continuous production of tetraalkoxysilanes are known, and essentially two methods are used in industry: The first method is the direct reaction of silicon powder with alcohol, while the second method is the esterification of tetrachlorosilane with alcohol.

The latter method, esterification of tetrachlorosilane with alcohol, can be conducted at normal pressure and without energy input in simple reactors. The ester mixture which is produced must be distilled, however, in order to remove, in particular, chlorine-containing impurities such as chlorine-containing esters and dissolved hydrogen chloride. The cost of such distillation is very high if one wishes to obtain a product tetraalkoxysilane of low chlorine content. For example, such distillation is conducted in a column having a large number of plates, in countercurrent distillation with alcohol. The residual chlorine in the tetraalkoxysilane product is neutralized in an additional reaction stage. The salt thereby obtained must be separated and appropriately discarded, and the tetraalkoxysilane must undergo additional distillative purification. Further, the esterification of tetrachlorosilane with alcohol involves the liberation of gaseous hydrogen chloride, which is costly to purify if it is to be economically recovered. The method essentially requires two reaction stages to convert the silicon to tetraalkoxysilane, viz. synthesis of the chlorosilane, and esterification of the chlorosilane. For more efficiency there is a need for a method employing only one reaction stage.

A method of producing alkoxysilanes in a single step reaction is the direct synthesis from silicon and alcohols. In U.S. Pat. No. 5,084,590, such a direct synthesis in the presence of a copper catalyst is described. However, the predominant product of this reaction is the trialkoxysilane. Where the objective of the direct synthesis is tetraalkoxysilanes, there is no known way of optimizing the reaction conditions which appreciably avoids formation of Si—H bonds and thereby formation of trialkoxysilanes. Accordingly, yields of tetraalkoxysilanes are unsatisfactory. Moreover, costly processing of the copper-containing residues is required, rendering the copper-catalyzed synthesis unsuitable for economical and efficient manufacture of tetraalkoxysilanes.

German 28 16 386 describes a catalytic method of manufacturing tetraalkoxysilanes from silicon and alcohols without the introduction of heavy metals such as copper. The catalysts comprise alkali alcoholate, ether alcohols and alkanolamines. Preferably, the method is conducted in a stirred vessel. The yield does not exceed 90 wt. %, based on the silicon introduced, which is not sufficiently high for an efficient continuous process. A side reaction of hydrogen with the alcohols occurs, forming water and alkanes, which necessitates a costly distillation with a scavenger, e.g., azeotropic distillation, in order to remove the water. The water present deactivates the catalyst and also leads to undesirable oligomerization of the tetraalkoxysilanes.

U.S. Pat. No. 4,288,604 describes a discontinuous method of reacting silicon and alcohols to form tetraalkoxysilanes in the presence of a basic catalyst. The silicon used must be comminuted under a nitrogen atmosphere in order to avoid blocking of the silicon surface with oxygen. In order to enable initiation of the reaction, inert, high-boiling solvents are employed. In addition, hydroxide scavengers must be employed in order to deactivate hydroxyl groups which are formed or which are introduced with reaction mixture components. Despite the use of appreciable amounts of inert solvents, hydroxide scavengers, and alkali alcoholates (as catalysts), the method is unsuitable for a continuous process, because it falls far short of the necessary high conversions of the silicon and ethanol to product. A need, therefore, continues to exist for a continuous process of producing tetraalkoxysilanes in high yield.

SUMMARY OF THE INVENTION

Accordingly, one object of the present invention is to provide a simple, continuous method of manufacturing chlorine-free tetraalkoxysilanes, which method enables direct reaction of metallic silicon powder and alcohols with improved selectivity and space-time yield of product.

Briefly, this object and other objects of the present invention as hereinafter will become more readily apparent can be attained by a continuous method of manufacturing chlorine-free tetraalkoxysilanes of formula (I)

$$(R^1O)_4Si \qquad (I)$$

wherein $R^1$ is, independently in each instance, an unbranched, branched, and/or cyclic $C_{1-6}$ hydrocarbon group, comprising:

reacting metallic silicon powder with a monohydric alcohol in the presence of a basic catalyst comprising a mixture of:

(a) at least one compound of formula (II)

$$[R^2O—(R^3O)_m]_nSi(OR^1)_{4-n} \qquad (II)$$

(b) at least one compound of formula (III)

$$R^2O—(R^3O)_m—M, \text{ and} \qquad (III)$$

(c) at least one compound of formula (IV)

$$R^2O—(R^3O)_m—H \qquad (IV)$$

wherein $R^1$ is as defined above;

$R^2$ represents, independently in each instance, a $C_{1-10}$ hydrocarbon group, or hydrogen;

$R^3$ represents, independently in each instance, a $C_{1-4}$ hydrocarbon group;

M represents an alkali metal selected from the group consisting of Li, Na, and K;

m is zero or a number in the range of 1–20; and n is zero or a number in the range of 1–4; further comprising:

charging said catalyst in advance to a continuously operating reactor to which at elevated temperature is also continuously added metallic silicon powder and the alcohol; and then separating the reaction mixture in a first column, in which gaseous hydrogen is discharged from the top, high-boiling catalyst is returned to the reaction mixture in said reactor, and low-boiling components are sent to a second separation column in which the tetraalkoxysilanes of formula (I) are separated, and low-boiling alcohol(s) present is/are turned to the reactor.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

the Figure is a flow diagram of a process embodiment of the invention for producing tetraalkoxysilane by the reaction of metallic silicon and an alcohol.

DETAILED DESCRIPTION OF THE PREFERRED EMBODIMENTS

Figure 1:
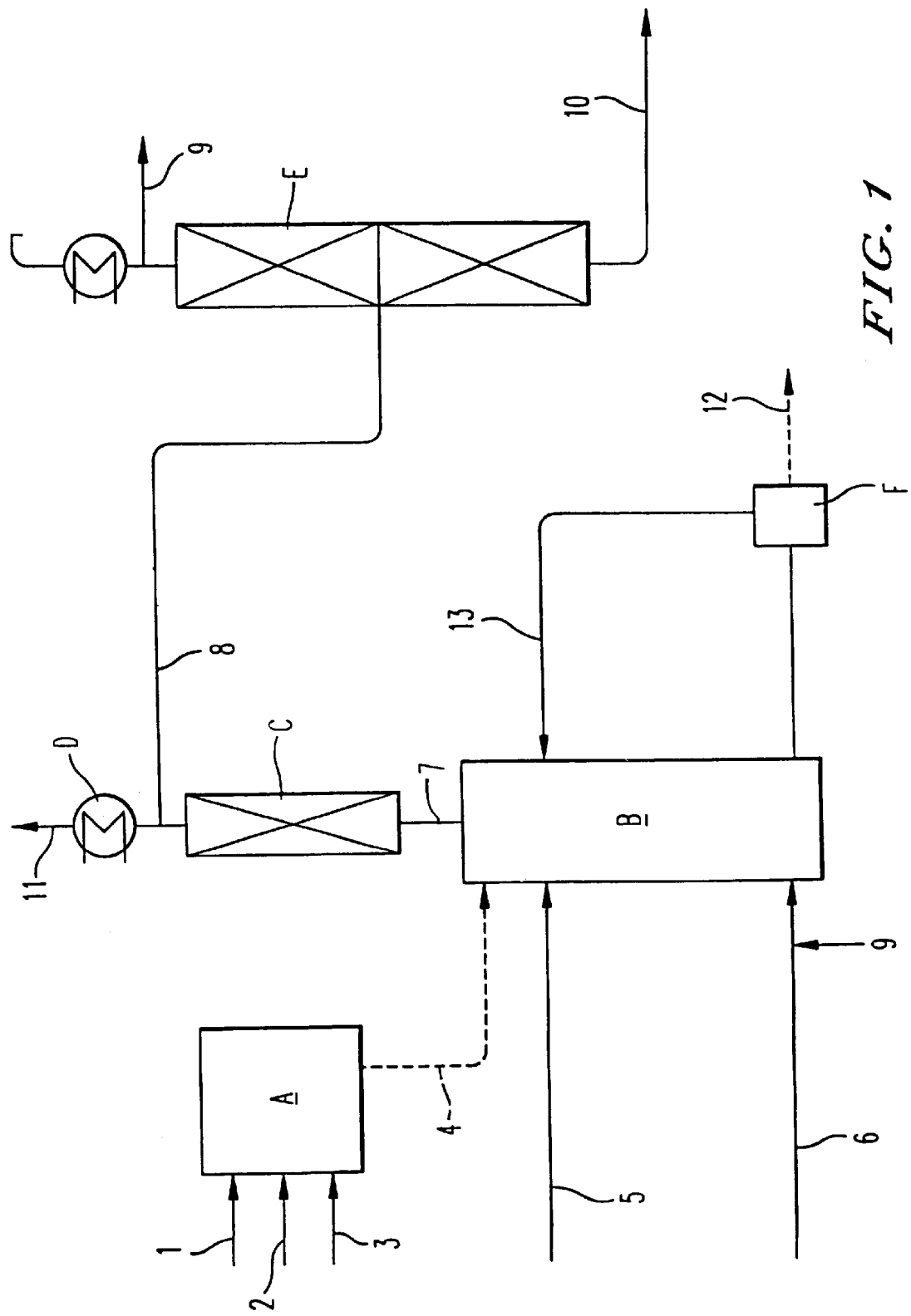

Silicon powder tends to be contaminated with such impurities as iron and other metals. Metallic silicon powder containing 10 wt. % iron can be used in the present process. In order to be able to maintain a continuous (steady-state) mode of operation, these contaminants must be withdrawn from the continuously operating reactor. The portions of reactive materials withdrawn along with the contaminants are recycled to the reactor after the contaminants have been removed. Suitable removal means for said contaminants include filters and centrifuges. In order to achieve high space-time yields, it is desirable to use silicon which is comminuted as finely as possible, e.g. with mean particle size less than 70 micron. The present method can accommodate mean particle sizes of 2 micron without problems. The method does not require comminution under conditions of exclusion of air, e.g. in a nitrogen atmosphere.

The alcohol(s) used include commercially available types such as methanol, ethanol and propanol. Anhydrous ethanol is preferred. Before entering the reactor the alcohol is heated; it may be fed to the continuous reactor while in liquid, boiling, or gaseous form.

In a preferred embodiment of the invention, the catalyst is prepared prior to (or upstream of) the silicon-alcohol reaction. In preparing the catalyst, the ratio of compounds IV:V:I is (2–3 mol IV):(1–2 mol V):(1 mol I) where formula (V) is $R_1OH$ and $R_1$ is as defined above. The alkali alcoholate (compound of formula V) and tetraalkoxysilane (compound of formula I) employed preferably contain the same alkoxy groups as the intended product of the process, and are selected from the groups methoxy, ethoxy, and propoxy. The alkali alcoholate of formula (V) can be used as a powder or dissolved in alcohol. Suitable alkali metals include lithium, sodium and potassium. The polyether alcohol compound (compound IV) is preferably selected from the group of substituted and/or unsubstituted polyethylene glycols. Particularly preferred is butyl diethylene glycol. A particularly preferred starting combination is: sodium ethylate, tetraethoxysilane, and butyl diethylene glycol.

The vessel employed for the catalyst preparation is a mixing reactor. Ordinarily, it is flushed with an inert gas such as nitrogen prior to introduction of the components. The reactor contents are preferably heated with stirring, to above 120° C., and possibly alcohol is removed by distillation. The reaction time is greater than 1 hr, preferably 2–3 hr and preferably at a reaction temperature of 140–160° C. Thereafter, alcohol which is formed is completely or partially removed by distillation, and the catalyst can be either stored in intermediate storage or introduced directly into the reactor in which the continuous reaction of metallic silicon powder and alcohol is being conducted.

In the continuously operated process, finely comminuted silicon and alcohol are reacted in the presence of the catalyst which has been prepared as described above. The reactors employed are 3-phase mixing reactors of the single-stage or multistage type. Particularly, preferred is a single-stage mixing reactor in which mixing can be by stirring, and/or by mixing-energy provided by the hydrogen being formed and by boiling reactants. The mixing-energy provided serves to uniformly distribute the silicon particles, which are of non-uniform particle size.

The reactor is charged with the catalyst mixture in the amount of 30–95 wt. %, preferably 65–75 wt. % and silicon powder in the amount of 5–70 wt. %, preferably 25–35 wt. %, based on the weight of the reaction mixture. If the catalyst introduced is alcohol-free, ordinarily alcohol is added prior to the start of the reaction, thereby introducing an excess of alcohol for the alcohol circulation loop. The reactor contents are heated to temperatures in the range 120–250° C., preferably in the range 190–200° C. When hydrogen begins to form, measured introduction of comminuted silicon and alcohol begins.

In the first column downstream of the reactor, the volatile components of the catalyst mixture are separated from the reaction products and the excess alcohol. The catalyst components removed are recycled to the reactor. The reflux ratio in this column is set depending on the number of plates. The hydrogen is discharged via the overhead condenser and other purification stages (if any), and the alcohol/tetraalkoxysilane mixture, which is obtained is continuously separated in another column. The excess alcohol which is separated is recycled to the reactor, as part of the circulation loop.

The liquid catalyst mixture is stable under the described conditions. No appreciable consumption of the catalyst is experienced.

Conversion rates achievable with the present method are greater than 0.8 mol Si/hr/liter reactor contents (and at least 0.3 mol/hr/liter), and a selectivity of 98% tetraalkoxysilane, based on the amount of silicon, can be achieved.

The present tetraalkoxysilane(s) product is/are chlorine-free and is, therefore, suitable for applications with very stringent requirements. The present product may be used in the production of high-purity glass and glass fibers, and as a raw material in coatings for semiconductor components.

General Manner of Implementation of the Invention

Referring to the Figure, an alkali alcoholate such as sodium ethylate (stream 1), polyether alcohol such as butyl diethylene glycol (stream 2), and tetraalkoxysilane such as tetraethoxysilane (stream 3) are charged into reactor A. The reaction mixture is heated to about 150° C. with stirring and possibly with removal of alcohol by distillation. Additional alcohol may be removed by distillation under vacuum. Following a processing time of at least 1 hr, the reaction mixture is cooled to below 50° C. The mixture may be sent to intermediate storage (with exclusion of air moisture) or may be introduced directly into reactor B (stream 4).

The prepared catalyst by stream 4 and comminuted silicon by stream 5 are introduced into reactor B. If the catalyst is alcohol-free, the excess alcohol needed for the alcohol recycle loop is also introduced. The reactor contents are then stirred and heated to 190–210° C.. The measured addition (dosing) of alcohol such as ethanol (stream 6) and silicon (stream 5) begins. When the formation of hydrogen (stream 11) is detected, the initiation of the reaction is established. After the first separation column C is heated by the vapors generated in reactor B entering therein by stream 7, the reflux below the head condenser D is adjusted such that the volatile catalyst components in stream 7 are retained. Thereafter the temperature in reactor B is kept constant. The impurities such as iron in the silicon metal are withdrawn from reactor B (stream 12), with the reactive components (stream 13) being returned to the reactor.

The alcohol/tetraalkoxysilane mixture which is discharged from separation column C (stream 8) is separated in the second separation column E, into alcohol such as ethyl alcohol (stream 9) and tetraalkoxysilane such as tetraethoxysilane (stream 10). The excess alcohol stream (stream 9) is recycled to reactor B, in the alcohol circulation loop.

Having generally described this invention, a further understanding can be obtained by reference to a specific example which is provided herein for purpose of illustration only and is intended to be limiting unless otherwise specified.

In order to produce a catalyst mixture, a heatable stirred reactor of 35 liter capacity was employed. The reactor was flushed with nitrogen following which 14.5 kg butyl diethylene glycol, 3.2 kg pulverulent sodium ethylate, and 9.6 kg 76% tetraethyoxysilane, dissolved in ethanol (streams 1–3), were charged to the reactor. The reactor contents were heated to 150° C. When the temperature in the reactor reached 118° C., the contents began to boil as a result of vaporization of ethanol which was present (including ethanol being formed). A 2 kg amount of ethanol was discharged at a head temperature of 78° C. under normal pressure. After 2.5 hr, no more distillate was being produced, and the pressure was reduced to 500 hPa. Within 1 hr, 1 kg ethanol had been removed by distillation. The reactor was then purged with nitrogen.

Reactor B was a bubble column with stirrers and a reaction volume of 10 liter. A 7 kg amount of catalyst (stream 4), and 3 kg comminuted silicon (stream 5) with a mean particle size $d_{50\%}=27$ micron were charged to the reactor. At 170° C. the reaction began. Thereafter the dosing of 3.5 mol/hr silicon (stream 6) and 34 mol/hr ethanol (stream 9) began. A 20 mol/hr amount of the ethanol was provided by recycle ethanol (stream 9). The temperature was increased to 190–200° C. and kept constant. High-boiling components (stream 7) were retained by means of the overhead column C, and the ethanol/tetraethoxysilane mixture (stream 8) was fractionated in column E, yielding tetraethoxysilane product in the amount of 3.5 mol/hr (stream 10). The ethanol (stream 9) was sent in dose amounts to reactor B, as excess ethanol. The impurities in the silicon powder (stream 12) were drawn off at the bottom of the reactor with other residual reactor contents and were collected in filter F, wherewith the liquid components (stream 13) were returned to the reactor.

The reaction was conducted such that in the steady-state conditions in reactor B the silicon concentration was maintained in the range 25–35 wt. %, and 65–75 wt. %, based on the weight of the reaction mixture. In steady-state operation, a space-time yield of 0.32 mol/liter/hr of tetraethoxysilane was obtained with a tetraethoxysilane selectivity of 98%, based on the silicon introduced.

German priority Application No. 198 04 731.2 filed Feb. 6, 1998 is hereby incorporated be reference into the present application.

Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by Letters Patent is:

1. A continuous method of manufacturing chlorine-free tetraalkoxysilanes of formula (I)

$$(R^1O)_4Si \qquad (I)$$

wherein $R^1$ is, independently in each instance, an unbranched, branched, and/or cyclic $C_{1-6}$ hydrocarbon group, comprising:
reacting metallic silicon powder with a monohydric alcohol in the presence of a basic catalyst comprising a mixture of:
(a) at least one compound of formula (II)

$$[R^2O-(R^3O)_m]_nSi(OR^1)_{4-n} \qquad (II)$$

(b) at least one compound of formula (III)

$$R^2O-(R^3O)_m-M, \text{ and} \qquad (III)$$

(c) at least one compound of formula (IV)

$$R^2O-(R^3O)_m-H \qquad (IV)$$

wherein $R^1$ is as defined above;
$R^2$ represents, independently in each instance, a $C_{1-10}$ hydrocarbon group, or hydrogen;
$R^3$ represents, independently in each instance, a $C_{1-4}$ hydrocarbon group;
M represents an alkali metal selected from the group consisting of Li, Na, and K;
m is zero or a number in the range of 1–20; and
n is zero or a number in the range of 1–4; further comprising:
charging said catalyst in advance to a continuously operating reactor to which at elevated temperature is also continuously added metallic silicon powder and the alcohol; and then
separating the reaction mixture in a first column, in which gaseous hydrogen is discharged from the top, high-boiling catalyst is returned to the reaction mixture in said reactor, and low-boiling components are sent to a second separation column in which the tetraalkoxysilanes of formula (I) are separated, and low-boiling alcohol(s) present is/are returned to the reactor;
wherein the catalyst is prepared by reacting at least one tetraalkoxysilane of formula (I)

$$(R^1O)_4Si \qquad (I)$$

with at least one compound of formula (IV)

$$R^2O-(R^3O)_m-H \qquad (IV)$$

and at one compound of formula (V)

$$R^1OM \qquad (V)$$

and the molar ratio of the compounds employed in preparing the catalyst is;
2–3 mol (IV) to 1–2 (V) to 1 mol (I).

2. The method according to claim 1, wherein $R^1$ is a methyl, ethyl, and/or propyl group.

3. The method according to claim 1, wherein the compound(s) of formula (IV) employed in preparing the catalyst is/are a substituted/or unsubstituted oligoethylene glycol and/or polyethylene glycol.

4. The method according to claim 1, wherein the catalyst is prepared at boiling temperature within the reactor for a time of at least 60 min.

5. The method according to claim 1, wherein the alcohol formed during the preparation of the catalyst is partially or completely discharged.

6. The method according to claim 1, wherein the alcohol (s) employed in preparing the tetraalkoxysilane(s) is/are methanol, ethanol and/or propanol.

7. The method according to claim 1, wherein the alcohol (s) is/are added as a liquid and/or as a gas.

8. The method according to claim 1, wherein said silicon is finely comminuted silicon having a mean particle size less than 70 micron.

9. The method according to claim 1, wherein the continuously operated reaction is conducted in a single-stage or multistage mixing reactor.

10. The method according to claim 9, wherein the reaction is conducted in a single-stage mixing reactor in the form of bubble column equipped with a stirrer.

11. The method according to claim 1, wherein the continuously operated reaction is operated within the temperature range of 120–250° C.

12. The method according to claim 1, wherein the catalyst present in the continuously operated reaction is present in the amount of 30–95 wt. %, based on the weight of the reaction mixture.

13. The method according to claim 12, wherein the amount of said catalyst ranges from 65–75 wt. %, based on the weight of the reaction mixture.

14. The method according to claim 1, wherein the metallic silicon powder present in the continuously operated reaction is present in the amount of 5–70 wt. %, based on the weight of the reaction mixture.

15. The method according to claim 14, wherein the amount of said metallic silicon powder ranges from 25–35 wt. %, based on the weight of the reaction mixture.

* * * * *